US011534109B2

(12) United States Patent
Divinsky et al.

(10) Patent No.: US 11,534,109 B2
(45) Date of Patent: Dec. 27, 2022

(54) SYSTEM AND METHOD FOR MAINTAINING SENSOR CONTACT

(71) Applicant: Nuvo Group Ltd., Tel Aviv (IL)

(72) Inventors: Ilya Divinsky, Ramat Gan (IL); Noga Weiss, Tel Aviv (IL); Oren Oz, Modiin (IL)

(73) Assignee: NUVO GROUP LTD., Tel Aviv (IL)

( * ) Notice: Subject to any disclaimer, the term of this patent is extended or adjusted under 35 U.S.C. 154(b) by 0 days.

(21) Appl. No.: 16/846,836

(22) Filed: Apr. 13, 2020

(65) Prior Publication Data

US 2020/0375536 A1    Dec. 3, 2020

Related U.S. Application Data

(63) Continuation of application No. 16/279,665, filed on Feb. 19, 2019, now Pat. No. 10,617,355.

(60) Provisional application No. 62/632,113, filed on Feb. 19, 2018.

(51) Int. Cl.
*A61B 5/00* (2006.01)
*A41D 1/00* (2018.01)
*A41D 1/21* (2018.01)

(52) U.S. Cl.
CPC ............ *A61B 5/6804* (2013.01); *A41D 1/002* (2013.01); *A61B 5/4343* (2013.01); *A41D 1/21* (2018.01); *A61B 5/6823* (2013.01); *A61B 2562/0204* (2013.01); *A61B 2562/04* (2013.01)

(58) Field of Classification Search
CPC . A61B 5/6804; A61B 5/4343; A61B 2562/04; A61B 5/6823; A61B 2562/0204; A41D 1/002
See application file for complete search history.

(56) References Cited

U.S. PATENT DOCUMENTS

| 7,789,836 B2 * | 9/2010 | Van Wyk | A61B 8/4227 600/459 |
| 2008/0287769 A1 * | 11/2008 | Kurzweil | A61B 5/25 600/509 |
| 2016/0270670 A1 * | 9/2016 | Oz | A61B 5/7203 |

* cited by examiner

*Primary Examiner* — Paula J Stice
(74) *Attorney, Agent, or Firm* — Greenberg Traurig, LLP (57) ABSTRACT

A garment includes a securing portion operable to removably secure the garment about an abdomen of a wearer; a sensor attachment portion pivotably attached to the securing portion, the sensor attachment portion including a sensor mount configured to receive and retain a sensor therein; and a sensor received in the flexible sensor mount; the securing portion and the sensor attachment portion being configured such that, when the securing portion is secured around the back of a wearer, the sensor attachment portion pivots with respect to the securing portion so as to self-position the sensor attachment portion across (a) an upper portion of the wearer's abdomen or (b) a lower portion of the wearer's abdomen; the flexible sensor mount being configured to orient a sensor received therein to be flush with skin of the wearer when the garment is worn by the wearer and to self-adjust during the course of pregnancy.

18 Claims, 12 Drawing Sheets

SYSTEM AND METHOD FOR MAINTAINING SENSOR CONTACT

CROSS-REFERENCE

This is a continuation of U.S. patent application Ser. No. 16/279,665, filed Feb. 19, 2019, which claims the benefit of commonly-owned U.S. Provisional Patent Application No. 62/632,113, filed Feb. 19, 2018, the contents of which are incorporated herein by reference in their entirety.

FIELD OF THE INVENTION

The invention relates generally to garments with integrated sensors.

BACKGROUND

Garments with integrated sensors for monitoring physical parameters of the wearer have a wide variety of applications, including monitoring physical parameters of both a pregnant mother and those of a fetus in utero.

SUMMARY

In an embodiment, a garment is a self-adjusting garment that is configured to be worn by a pregnant human subject during a course of pregnancy and to self-adjust positioning of at least one sensor integrated into the garment during the course of pregnancy; the garment includes a securing portion operable to removably secure the garment about an abdomen of a wearer; at least one sensor attachment portion pivotably attached to the securing portion, each of the at least one sensor attachment portion including at least one sensor mount configured to receive and retain a sensor therein; and at least one sensor, each of the at least one sensor being received in a corresponding one of the at least one flexible sensor mount of the at least one sensor attachment portion; the securing portion and the at least one sensor attachment portion are configured such that, when the securing portion is secured around the back of a wearer, the at least one sensor attachment portion pivots with respect to the securing portion so as to self-position the at least one sensor attachment portion across (a) an upper portion of the wearer's abdomen or (b) a lower portion of the wearer's abdomen, and each of the at least one flexible sensor mount is configured so as to orient a sensor received therein so as to be continuously flush with skin of the wearer when the garment is worn by the wearer and self-adjusts during the course of pregnancy.

In an embodiment, the at least one sensor includes at least one electrode. In an embodiment, the at least one sensor includes at least one acoustic sensor.

In an embodiment, the at least one sensor attachment portion includes two sensor attachment portions. In an embodiment, a first one of the sensor attachment portions is configured to extend around an upper portion of the abdomen of the wearer and a second one of the sensor attachment portions is configured to extend around a lower portion of the abdomen of the wearer.

In an embodiment, each of the sensor attachment portions includes a plurality of the flexible sensor mounts, wherein the at least one sensor includes a plurality of sensors, and wherein each of the plurality of sensors is received within a corresponding one of the plurality of flexible sensor mounts. In an embodiment, each of the sensor attachment portions includes five sensor mounts.

In an embodiment, the garment also includes at least one hinge, each of the at least one hinge connecting an end of the securing portion to an end of the at least one sensor attachment portion. In an embodiment, the at least one hinge includes a sensor. In an embodiment, the at least one hinge includes two hinges, wherein a first one of the hinges connects a first end of the securing portion to a first end of the at least one sensor attachment portion, and wherein a second one of the hinges connects a second end of the securing portion to a second end of the at least one sensor attachment portion. In an embodiment, the at least one sensor attachment portion includes two sensor attachment portions, wherein the first one of the hinges connects a first end of the securing portion to (a) a first end of a first one of the sensor attachment portions and (b) a first end of a second one of the sensor attachment portions, and wherein a second one of the hinges connects a second end of the securing portion to (a) a second end of a first one of the sensor attachment portions and (b) a second end of a second one of the sensor attachment portions.

In an embodiment, at least one of the at least one flexible sensor mount includes a flexible portion including an elastomeric material. In an embodiment, the elastomeric material has a spring coefficient of between 1 N/mm and 20 N/mm. In an embodiment, the at least one of the at least one sensor mount includes a rigid portion positioned within an opening in the flexible portion, the rigid portion configured to receive one of the at least one sensor therein. In an embodiment, each of the at least one sensor mount is configured to orient a sensor received therein so as to be flush with the skin of the wearer.

In an embodiment, method for positioning at least one sensor so as to be flush with skin on an abdomen of a wearer includes providing a garment including: a securing portion operable to removably secure the garment about an abdomen of a wearer; at least one sensor attachment portion pivotably attached to the securing portion, each of the at least one sensor attachment portion including at least one flexible sensor mount configured to receive and retain a sensor therein; at least one sensor, each of the at least one sensor being received in a corresponding one of the at least one flexible sensor mount of the at least one sensor attachment portion; wherein the securing portion and the at least one sensor attachment portion are configured such that, when the securing portion is secured about the back of a wearer, the at least one sensor attachment portion pivots with respect to the securing portion so as to extend around (a) an upper portion of the wearer's abdomen or (b) a lower portion of the wearer's abdomen, and wherein each of the at least one sensor mount is configured so as to orient a sensor received therein so as to be flush with skin of the wearer when the garment is worn by the wearer; positioning the garment so as to encircle a midsection of the wearer such that the securing portion extends around a back of the wearer and the at least one sensor attachment portion extends around an abdomen of the wearer; securing the securing portion so as to retain the garment encircling the midsection of the wearer, whereby the at least one sensor attachment portion is positioned around one of an upper portion of an abdomen of the wearer and a lower portion of an abdomen of the wearer, and whereby the at least one flexible sensor mount flexes so as to allow the one of the at least one sensor received therein to be positioned flush with skin of the wearer.

In an embodiment, the at least one sensor attachment portion includes two sensor attachment portions, and, when the securing portion is secured, a first one of the sensor attachment portions is positioned around an upper portion of the abdomen of the wearer and a second one of the sensor attachment portions is positioned around a lower portion of an abdomen of the wearer.

In an embodiment, the wearer is a pregnant human. In an embodiment, the at least one sensor includes ten sensors. In an embodiment, the at least one sensor includes at least one electrode and at least one acoustic sensor.

In some embodiments, a device includes a garment having a securing portion and a sensor attachment portion, the securing portion and the sensor attachment portion being movably attached to one another such that the securing portion is configured to remain in a fixed portion with respect to the wearer and the sensor attachment portion is configured to rotate with respect to the securing portion, at least one sensor being movably coupled to the sensor attachment portion such that, when the sensor attachment portion is positioned adjacent to the wearer's skin, the at least one sensor deflects so as to be positioned flush with the wearer's skin In some embodiments, a method for maintaining sensor contact includes providing a garment having a securing portion and a sensor attachment portion, the sensor attachment portion being movably attached to one another such that the securing portion is configured to remain in a fixed portion with respect to the wearer and the sensor attachment portion is configured to rotate with respect to the securing portion, at least one sensor being movably coupled to the sensor attachment portion such that, when the sensor attachment portion is positioned adjacent to the wearer's skin, the at least one sensor deflects so as to be positioned flush with the wearer's skin, the method further comprising donning the garment by a wearer, whereby the at least one sensor attachment portion deflects so as to position the at least one sensor in proximity to the wearer's skin, and whereby the at least one sensor deflects so as to be positioned flush with the wearer's skin.

DETAILED DESCRIPTION

Among those benefits and improvements that have been disclosed, other objects and advantages of this invention will become apparent from the following description taken in conjunction with the accompanying figures. Detailed embodiments of the present invention are disclosed herein; however, it is to be understood that the disclosed embodiments are merely illustrative of the invention that may be embodied in various forms. In addition, each of the examples given in connection with the various embodiments of the invention which are intended to be illustrative, and not restrictive.

Throughout the specification and claims, the following terms take the meanings explicitly associated herein, unless the context clearly dictates otherwise. The phrases "in one embodiment," "in an embodiment," and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention.

As used herein, the term "based on" is not exclusive and allows for being based on additional factors not described, unless the context clearly dictates otherwise. In addition, throughout the specification, the meaning of "a," "an," and "the" include plural references. The meaning of "in" includes "in" and "on."

As used herein the term "contact region" encompasses the contact area between the skin of a pregnant human subject and a sensor positioned against the skin such that the sensor can sense physiological parameters of the pregnant human subject (e.g., electrical current suitable for electrocardiogram data, acoustic signals suitable for phonocardiogram data, etc.).

In some embodiments, the present invention provides a system including a garment and at least one sensor mounted to the garment, the garment and the at least one sensor configured such that, when the garment is worn by a wearer, the position and orientation of at least a portion of the garment and the position and orientation of the at least one sensor adjust so as to provide a suitable contact region for the at least one sensor. In some embodiments, the garment is a belt. In some embodiments, the at least one sensor is an electrode. In some embodiments, the at least one sensor is an acoustic sensor. In some embodiments, the at least one sensor is a position sensor. In some embodiments, the at least one sensor is a motion sensor. In some embodiments, the at least one sensor is an optical sensor. In some embodiments, that at least one sensor is any other type of sensor that, when in use, is to be positioned adjacent to a subject's abdomen in a manner so as to provide a suitable contact area between the sensor and the subject's abdomen. In some embodiments, the garment includes a securing portion configured to remain in a fixed position with respect to the wearer and at least one sensor attachment portion configured to rotate with respect to the securing portion. In some embodiments, the at least one sensor is mounted to the at least one sensor attachment portion and is configured to rotate with respect to the at least one sensor attachment portion.

In some embodiments, the present invention provides a method for maintaining a sensor that is mounted to a garment in contact with a wearer's skin. In some embodiments, a method includes providing a garment having a securing portion and a sensor attachment portion, the sensor attachment portion being movably attached to one another such that the securing portion is configured to remain in a fixed portion with respect to the wearer and the sensor attachment portion is configured to rotate with respect to the securing portion, at least one sensor being movably coupled to the sensor attachment portion such that, when the sensor attachment portion is positioned adjacent to the wearer's skin, the at least one sensor deflects so as to be positioned flush with the wearer's skin, the method further comprising donning the garment by a wearer, whereby the at least one sensor attachment portion deflects so as to position the at least one sensor in proximity to the wearer's skin, and whereby the at least one sensor deflects so as to be positioned flush with the wearer's skin.

Figure 1:
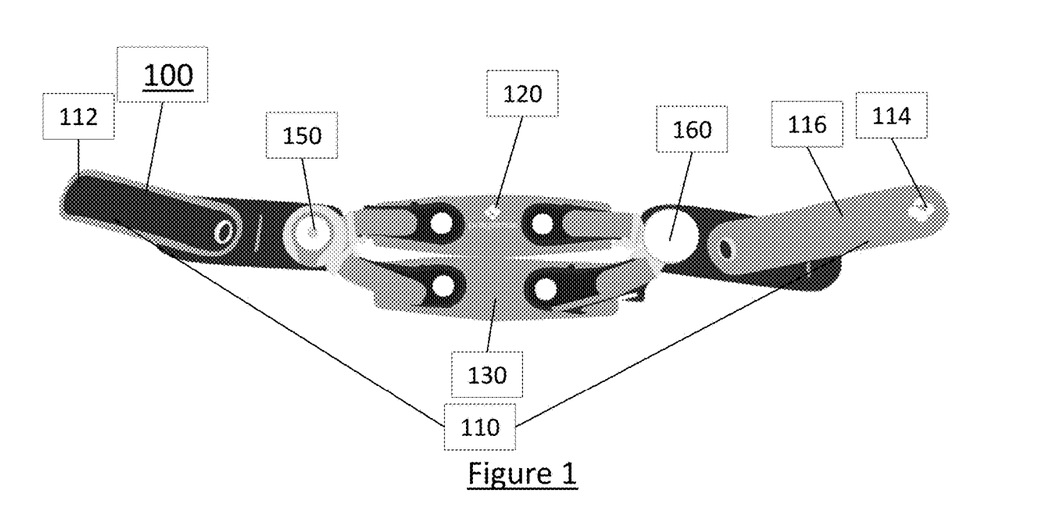
FIG. 1 shows a front view of a garment according to an exemplary embodiment.
Figure 2:
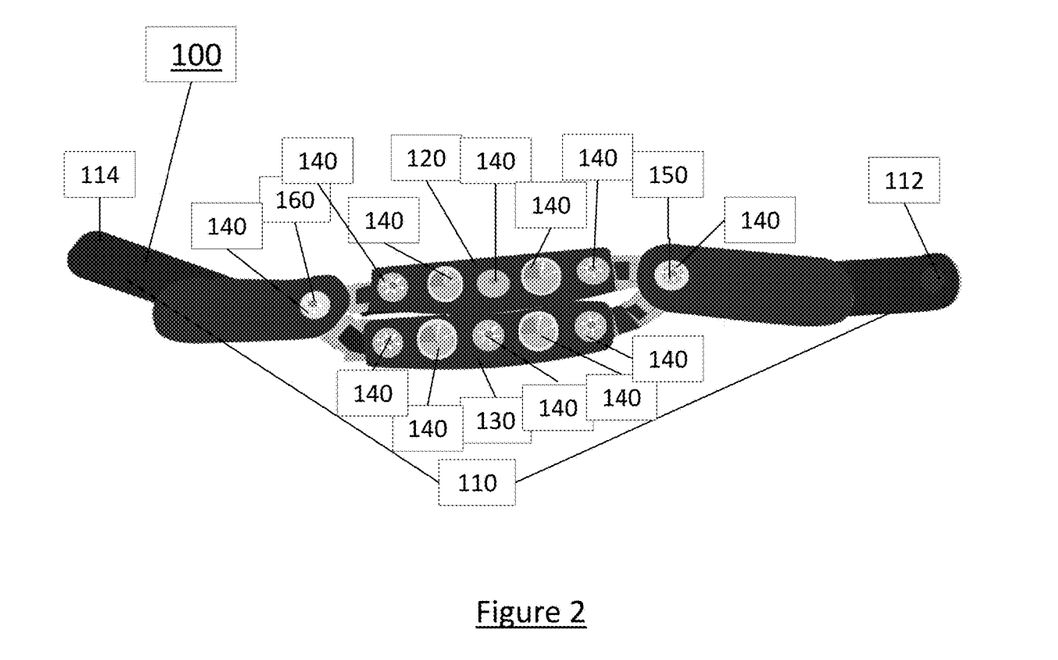
FIG. 2 shows a rear view of the garment of FIG. 1.

FIGS. 1 and 2 show a front view and a rear view, respectively, of a garment 100 according to some embodiments of the present invention. In some embodiments, the garment 100 is a belt. In some embodiments, the garment 100 includes a securing portion 110. In some embodiments, the securing portion 110 includes a first side 112 and a second side 114 that are configured to engage one another. In some embodiments, the securing portion 110 includes a strap 116. In some embodiments, the securing portion 110 is configured to secure the garment 100 to the wearer's body at or near the wearer's waist. In some embodiments, the length of the securing portion 110 is adjustable (e.g., through the use of buckles, straps, or other similar mechanisms).

Continuing to refer to FIGS. 1 and 2, in some embodiments, the garment 100 includes a first sensor attachment portion 120 and a second sensor attachment portion 130. In some embodiments, other than insofar as they are positioned differently within the garment 100, the first and second sensor attachment portions 120, 130 are substantially similar to one another.

Continuing to refer to FIGS. 1 and 2, in some embodiments, each of the first and second sensor attachment portions 120, 130 includes a plurality of sensors 140. In some embodiments, the sensors 140 include at least one sensor of a first type of sensor and at least one sensor of a second type of sensor. In some embodiments, the sensors 140 include more than two types of sensors (e.g., three types of sensors, four types of sensors, five types of sensors, etc.). In some embodiments, the first type of sensor is an acoustic sensor. In some embodiments, the second type of sensor is an electrode (e.g., a bio-potential sensor, which may be either wet or dry).

Continuing to refer to FIGS. 1 and 2, in some embodiments, each of the first and second sensor attachment portions 120, 130 has a first end and a second end, is joined to a first end of the securing portion 110 by a first hinge portion 150 at the respective first ends of the first and second sensor attachment portions 120, 130, and is joined to a second end of the securing portion 110 by a second hinge portion 160 at the respective second ends of the first and second sensor attachment portions 120, 130. In some embodiments, the lengths of the first and second sensor attachment portions 12, 130 are adjustable (e.g., through the use of buckles, straps, or other similar mechanisms). In some embodiments, one of the sensors 140 is integrated into each of the first and second hinge portions 150, 160.

Figure 3:
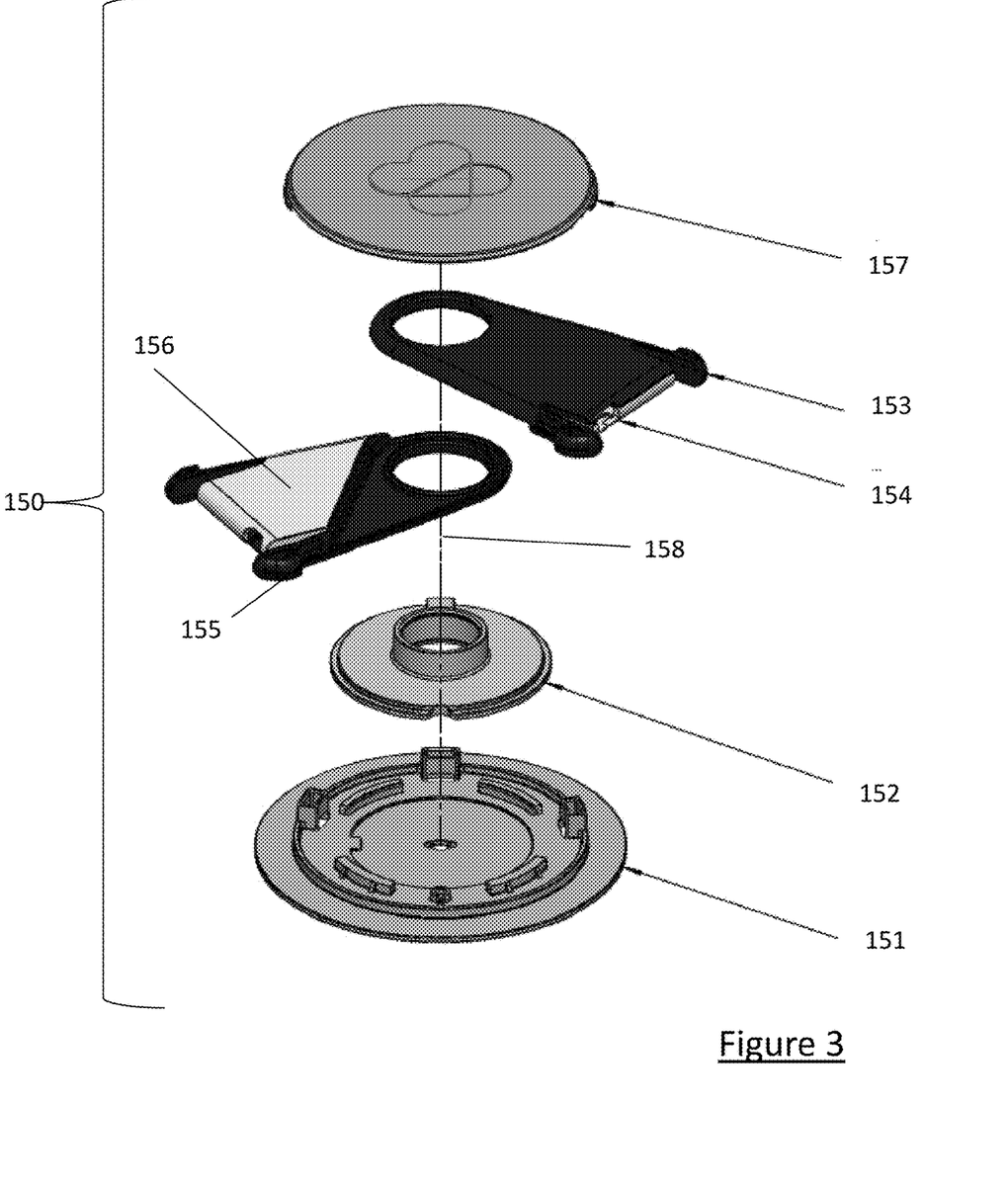
FIG. 3 shows an exploded view of a hinge portion according to an exemplary embodiment.
Figure 12A:
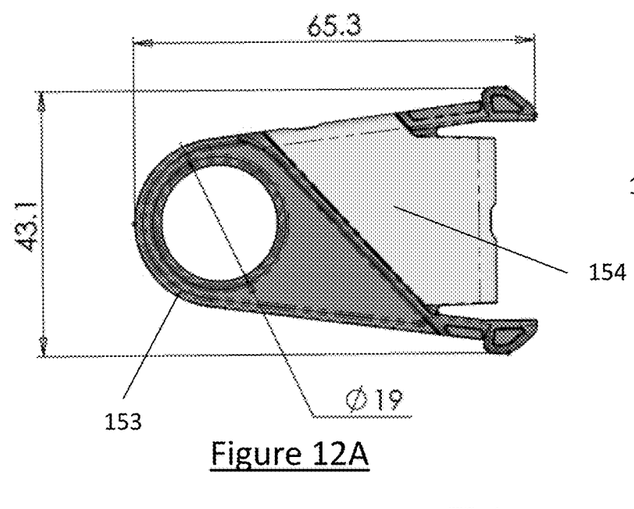
FIG. 12A shows a front view of an embodiment of an assembled hook including a hook top portion and a hook bottom portion, with exemplary dimensions being included therein.
Figure 12B:
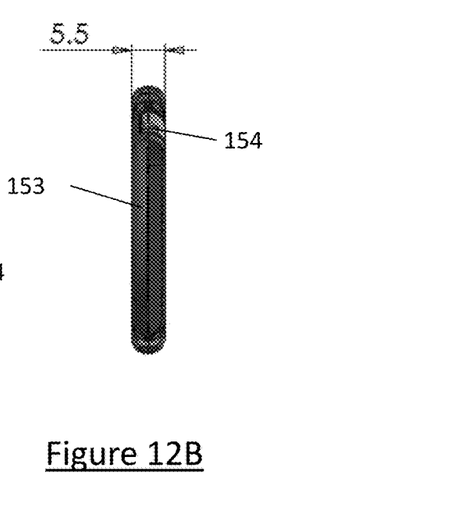
FIG. 12B shows a side view of the hook of FIG. 12A, with exemplary dimensions being included therein.

FIG. 3 shows an exploded view of the first hinge portion 150. In some embodiments, other than insofar as they are positioned differently within the garment 100, the first and second hinge portions 150, 160 are substantially similar to one another, and, therefore, only the first hinge portion 150 will be described in detail herein. In some embodiments, the first hinge portion 150 includes a base 151, an axis cover 152, a first hook including a first hook top portion 153 and a first hook bottom portion 154, a second hook including a second hook top portion 155 and a second hook bottom portion 156, and a cover 157. FIG. 12A shows a front view of the assembled first hook top portion 153 and the first hook top portion 154, with dimensions thereof in millimeters included. FIG. 12B shows a side view of the assembled first hook top portion 153 and the first hook bottom portion 154, with dimensions thereof in millimeters included.

Continuing to refer to FIG. 3, The elements of the first hinge portion 150 are oriented about a rotational axis 158, which, it will be it apparent to those of skill in the art, is an imaginary feature defined herein for the purpose of describing the first hinge portion 150, and not a physical element of the first hinge portion 150. In some embodiments, the first hook top portion 153 and the second hook top portion 155 are positioned on the axis cover 152, and are configured so as to be able to rotate about the rotational axis 158 with respect to the axis cover 152 and with respect to one another. In some embodiments, the first hook top portion 153 and the second hook top portion 155 include stops configured to define a closest possible angular displacement of the first hook top portion 153 and the second hook top portion 155 with respect to one another. In some embodiments, the cover 157 includes stops configured to define a furthest possible angular displacement of the first hook top portion 153 and the second hook top portion 155 with respect to one another. In some embodiments, the first hook top portion 153 and the first hook bottom portion 154 define a strain relief therebetween through which wires may pass. In some embodiments, the second hook top portion 155 and the second hook bottom portion 156 define a strain relief therebetween through which wires may pass. In some embodiments, each of the first and second hooks includes a buckle 159. The buckles 159 are configured to adjustably attach to the first and second sensor attachment portions 120, 130 in accordance with known techniques.

Figure 13A:
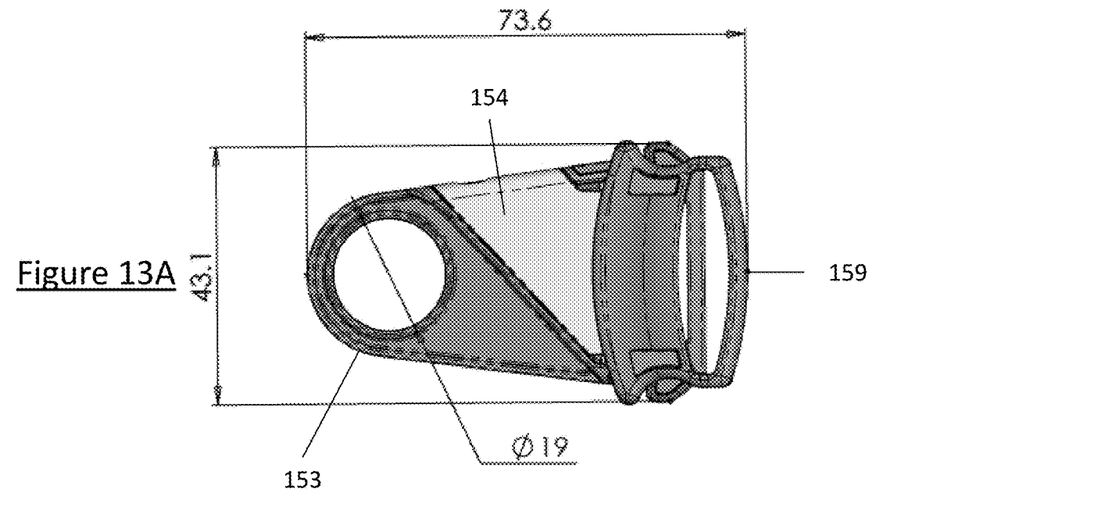
FIG. 13A shows a front view of an embodiment of an assembled hook including a hook top portion, a hook bottom portion, and a buckle, with exemplary dimensions being included therein.
Figure 13B:
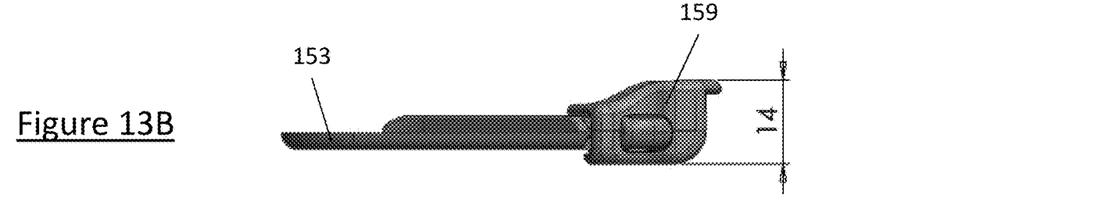
FIG. 13B shows a top view of the buckle of FIG. 13A, with exemplary dimensions being included therein.
Figure 14A:
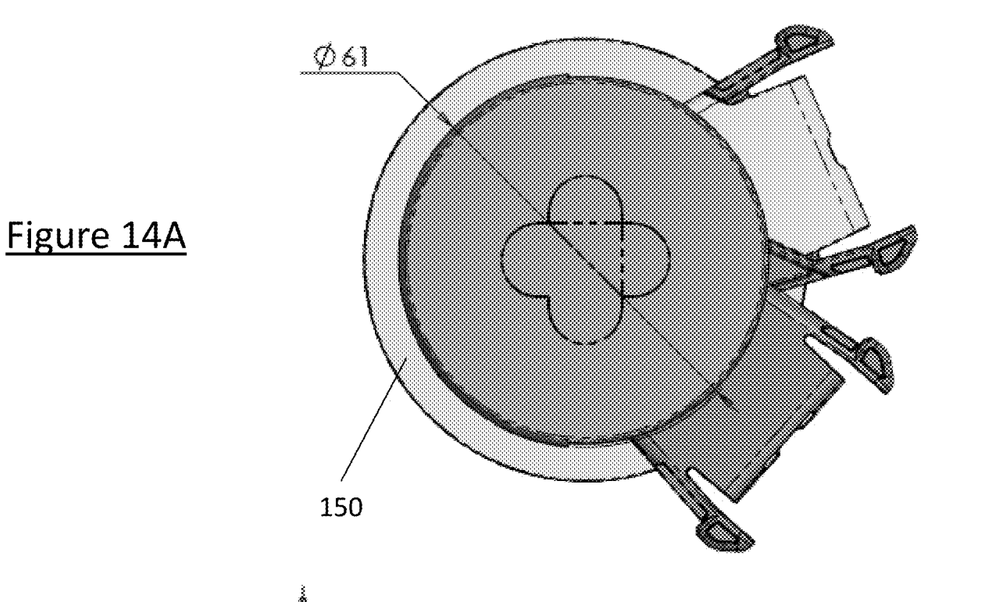
FIG. 14A shows a front view of an embodiment of a hinge portion with exemplary dimensions being included therein.
Figure 14B:
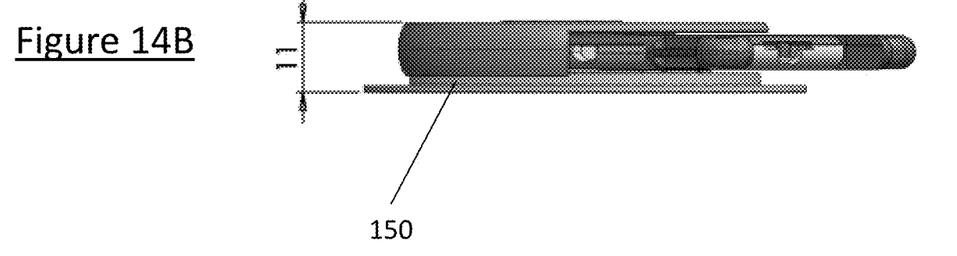
FIG. 14B shows a top view of the hinge portion of FIG. 14A with exemplary dimensions being included therein.
Figure 15A:
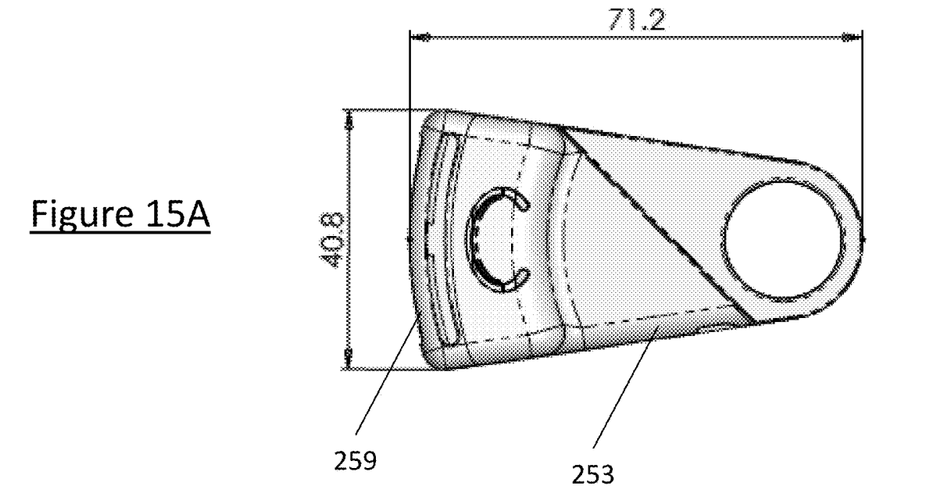
FIG. 15A shows a front view of an embodiment of an assembled hook with exemplary dimensions being included therein.
Figure 15B:
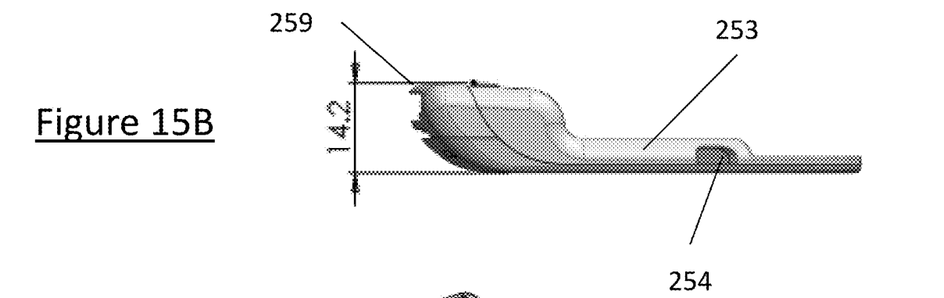
FIG. 15B shows a top view of the hook of FIG. 15A with exemplary dimensions included therein.
Figure 15C:
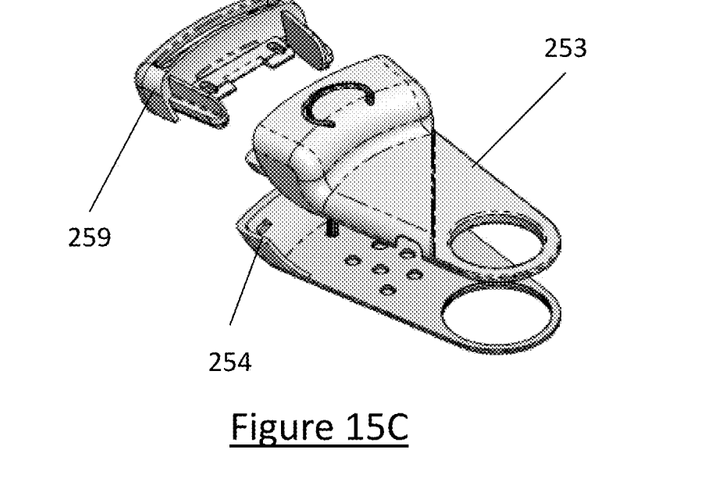
FIG. 15C shows an exploded view of the hook of FIG. 15A.

FIG. 13A shows a front view of the first hook top portion 153, the first hook bottom portion 154, and the buckle 159, with dimensions thereof in millimeters included. FIG. 13B shows a top view of the first hook top portion 153, the first hook bottom portion 154, and the buckle 159, with dimensions thereof in millimeters included. FIG. 14A shows a front view of the assembled first hinge portion 150, with dimensions thereof in millimeters included. FIG. 14B shows a top view of the assembled first hinge portion 150, with dimensions thereof in millimeters included. FIG. 15A shows a front view of another embodiment of a first hook including a first hook top portion 253, a first hook bottom portion 254, and a buckle 259, with dimensions thereof in millimeters included. FIG. 15B shows a side view of the embodiment of the first hook of FIG. 15A including the first hook top portion 253, the first hook bottom portion 254, and the buckle 259, with dimensions thereof in millimeters included. FIG. 15C shows an exploded view of the embodiment of the first hook of FIG. 15A including the first hook top portion 253, the first hook bottom portion 254, and the buckle 259.

Figure 4:
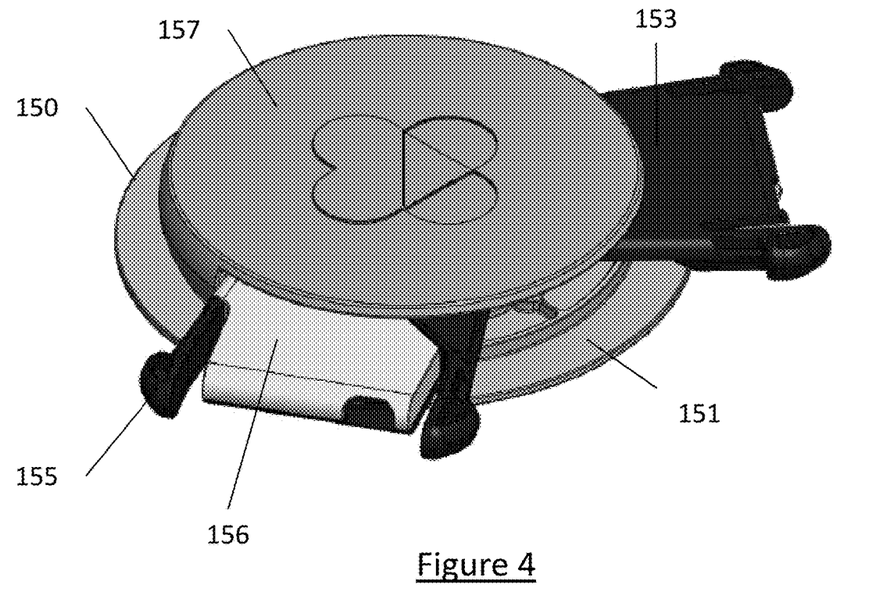
FIG. 4 shows an assembled view of the hinge portion of FIG. 3, the hinge portion being positioned in a first orientation.
Figure 5:
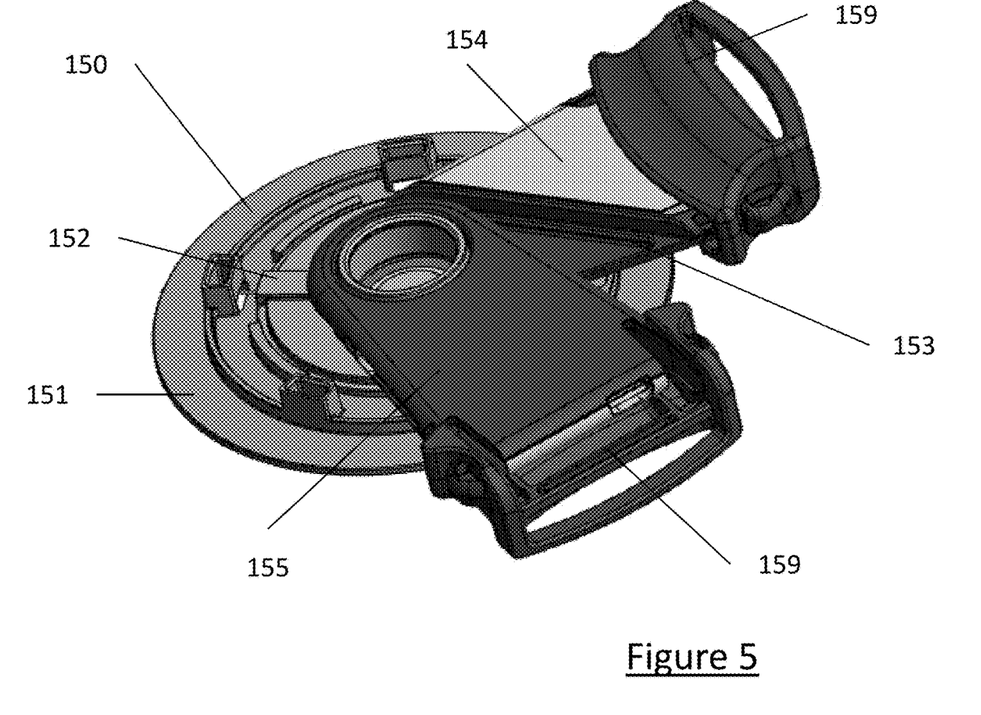
FIG. 5 shows the hinge portion of FIG. 4, a cover being removed to expose elements of the hinge portion, the hinge portion being positioned in a second orientation.

FIG. 4 shows an assembled view of the first hinge portion 150, the first and second hook top portions 153, 155 being positioned as far from one another as allowed by stops of the cover 157. FIG. 5 shows an assembled view of the first hinge portion 150, the cover 157 being removed to show the remaining elements of the first hinge portion 150, the first and second hook top portions 153, 155 being positioned closer to one another than in the position shown in FIG. 4, but not abutting one another as defined by their respective stops. In some embodiments, the first and second hinge portions 150, 160 are configured such that, when their respective hook portions are at their closest angular displacement with respect to one another, the first and second sensor attachment portions 120, 130 are positioned with respect to one another so as to fit a pregnant mother having an abdomen circumference of 50 centimeters. In some embodiments, the first and second hinge portions 150, 160 are configured such that, when their respective hook portions are at their closest angular displacement with respect to one another, the first and second sensor attachment portions 120, 130 are positioned with respect to one another so as to fit a pregnant mother having an abdomen circumference of 55 centimeters. In some embodiments, the first and second hinge portions 150, 160 are configured such that, when their respective hook portions are at their closest angular displacement with respect to one another, the first and second sensor attachment portions 120, 130 are positioned with respect to one another so as to fit a pregnant mother having an abdomen circumference of 60 centimeters. In some embodiments, the first and second hinge portions 150, 160 are configured such that, when their respective hook portions are at their furthest angular displacement with respect to one another, the first and second sensor attachment portions 120, 130 are positioned with respect to one another so as to fit a pregnant mother having an abdomen circumference of 120 centimeters. In some embodiments, the first and second hinge portions 150, 160 are configured such that, when their respective hook portions are at their furthest angular displacement with respect to one another, the first and second sensor attachment portions 120, 130 are positioned with respect to one another so as to fit a pregnant mother having an abdomen circumference of 125 centimeters. In some embodiments, the first and second hinge portions 150, 160 are configured such that, when their respective hook portions are at their furthest angular displacement with respect to one another, the first and second sensor attachment portions 120, 130 are positioned with respect to one another so as to fit a pregnant mother having an abdomen circumference of 130 centimeters.

Figure 6:
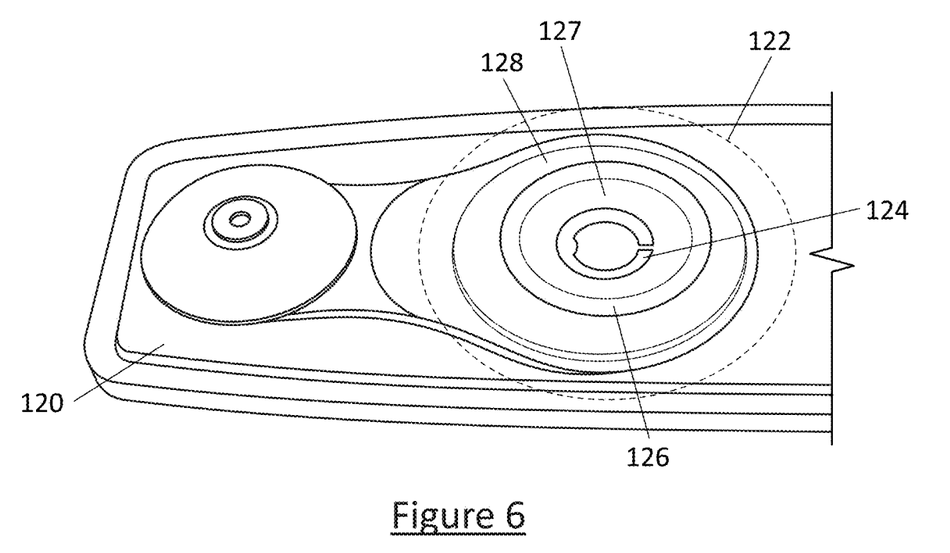
FIG. 6 shows a sensor mount according to an exemplary embodiment.
Figure 16A:
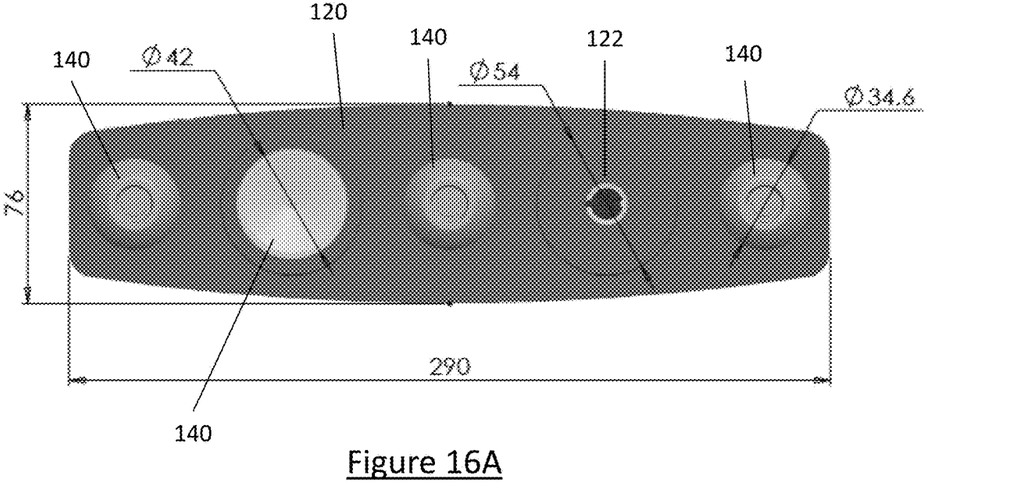
FIG. 16A shows a rear view of an embodiment of a sensor attachment portion with sensors mounted thereon, with exemplary dimensions included therein.
Figure 16B:
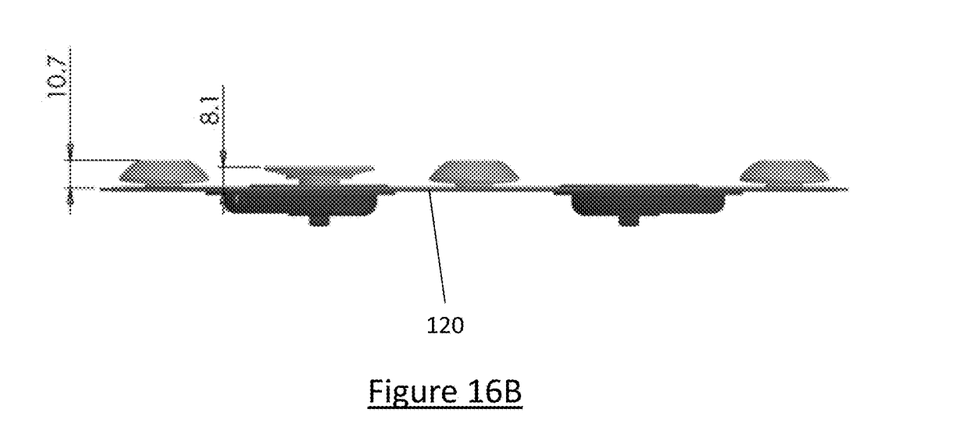
FIG. 16B shows a top view of the sensor attachment portion with sensors mounted thereon of FIG. 16A, with exemplary dimensions included therein.

FIG. 6 shows a portion of the first sensor attachment portion 120. In some embodiments, each of the first sensor attachment portion 120 and the second sensor attachment portion 130 includes at least one flexible sensor mount 122, although only the first sensor attachment portion 120 is specifically illustrated in detail herein. In some embodiments, the flexible sensor mount 122 includes a rigid portion 124 positioned within a flexible portion 126. In some embodiments, the flexible portion 126 includes an inner region 127 that surrounds the rigid portion 124 and an outer region 128 that joins the remainder of the first sensor attachment portion 120. In some embodiments, the rigid portion 124 is formed from a metal. In some embodiments, the rigid portion 124 is formed from a plastic. In some embodiments, the rigid portion 124 is formed from another rigid material. In some embodiments, the flexible portion 126 is formed from an elastomeric material. In some embodiments, the flexible portion 126 is formed from silicone. In some embodiments, the flexible portion 126 is formed from another durable, flexible material. FIG. 16A shows a rear view of the first sensor attachment portion 120 with four (5) sensors 140 installed therein and one of the fixable sensor mounts 122 exposed, with dimensions thereof in millimeters included. FIG. 16B shows a top view of the first sensor attachment portion 120 as shown in FIG. 16A, with dimensions thereof in millimeters included. In some embodiments, the flexible portion 126 of the flexible sensor mount 122 is stretchable so as to provide suitable contact between a sensor housed therein and the curved profile of the skin of a subject's abdomen. In some embodiments, the flexible portion 126 is stretchable with a spring coefficient of between 1 N/mm and 20 N/mm. In some embodiments, the flexible portion 126 is stretchable with a spring coefficient of between 1 N/mm and 15 N/mm. In some embodiments, the flexible portion 126 is stretchable with a spring coefficient of between 1 N/mm and 10 N/mm. In some embodiments, the flexible portion 126 is stretchable with a spring coefficient of between 1 N/mm and 7.5 N/mm. In some embodiments, the flexible portion 126 is stretchable with a spring coefficient of between 1 N/mm and 20 5/mm. In some embodiments, the flexible portion 126 is stretchable with a spring coefficient of between 1 N/mm and 4 N/mm. In some embodiments, the flexible portion 126 is stretchable with a spring coefficient of between 1 N/mm and 3 N/mm. In some embodiments, the flexible portion 126 is stretchable with a spring coefficient of between 1 N/mm and 2 N/mm. In some embodiments, the flexible portion 126 is stretchable with a spring coefficient of between 1 N/mm and 1.5 N/mm. In some embodiments, the flexible portion 126 is stretchable with a spring coefficient of about 1.25 N/mm. In some embodiments, the flexible portion 126 is stretchable with a spring coefficient of 1.25 N/mm. In some embodiments, the flexible sensor mount is made from a viscoelastic material that conforms to the Kelvin-Voigt model.

Figure 17:
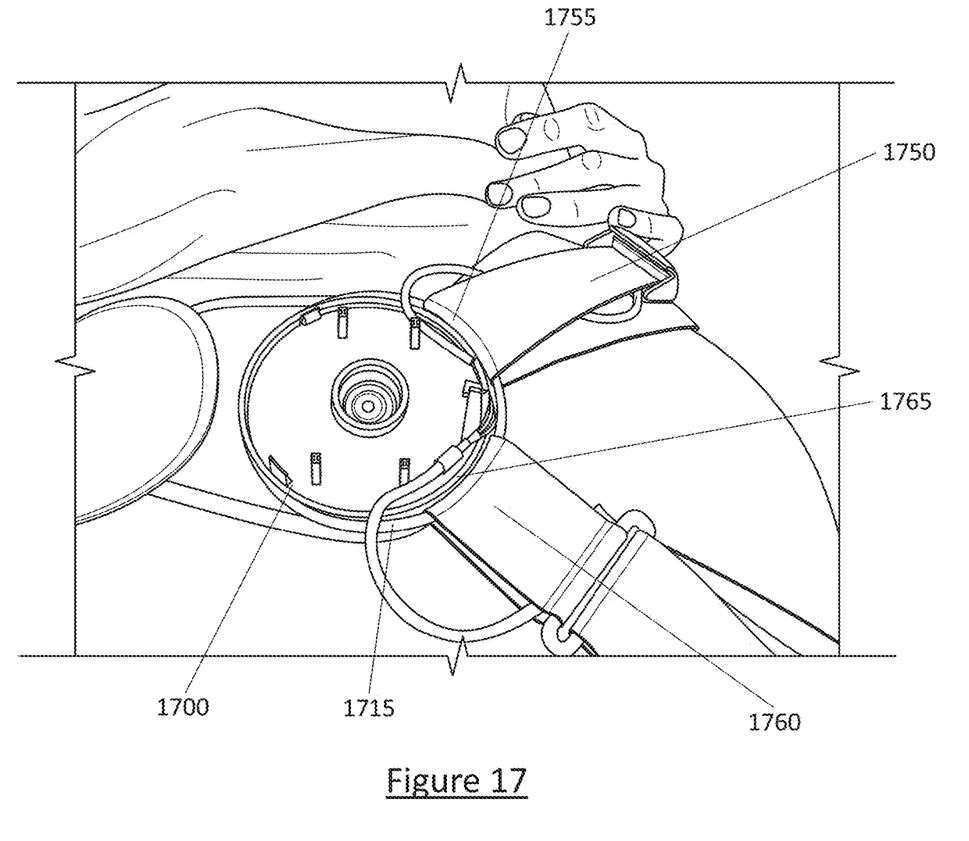
FIG. 17 shows a perspective view of an embodiment of a hinge portion.

FIG. 17 shows a perspective view of another embodiment of a hinge portion 1700 along with portions of another embodiment of sensor attachment portions 1750 and 1760. The hinge portion 1700 includes a circular base 1710 having a ring 1715 extending around a portion of its perimeter. In some embodiments, the sensor attachment portions 1750 and 1760 include respective loop portions 1755 and 1765 that loop around the ring 1715 in a manner such that the sensor attachment portions 1750 and 1760 may pivot about the hinge portion 1700 in order that the sensor attachment portions 1750 and 1760 follow the contours of the abdomen of the wearer, as described herein.

Figure 18:
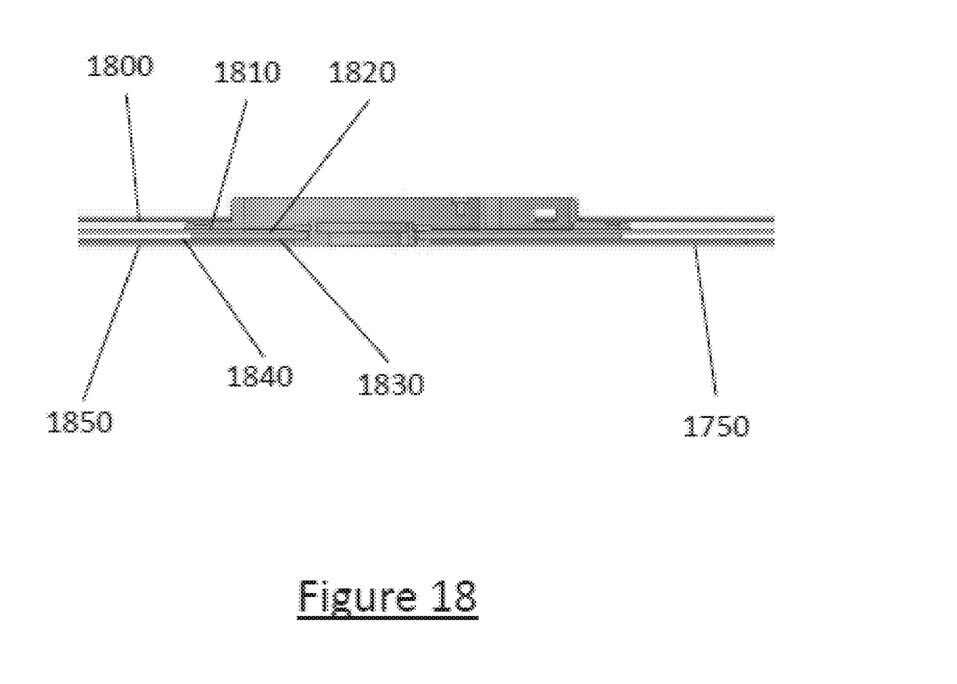
FIG. 18 shows a top view of an embodiment of a sensor attachment portion.

FIG. 18 shows a top view of a portion of the sensor attachment portion 1750. The sensor attachment portion 1750 is surrounded by a multi-layered structure including a first fabric layer 1800, a second fabric layer 1810, a flexible printed circuit board 1820, an elastic polymer sheet 1830, a third fabric layer 1840, and a fourth fabric layer 1850. In some embodiments, the sensor attachment portion 1750 is configured such that the first fabric layer 1800 faces the skin of the wearer when a garment including the sensor attachment portion 1750 is worn. In some embodiments, the first fabric layer 1800 and the fourth fabric layer 1850 include a coated elastic fabric. In some embodiments, the elastic fabric includes a polyether-polyurea copolymer such as that commercialized under the trademark LYCRA® by E. I. du Pont de Nemours Company of Wilmington, Del. In some embodiments, the elastic fabric is coated with thermoplastic polyurethane ("TPU"). In some embodiments, the second fabric layer 1810 and the third fabric layer 1840 include a stiff woven fabric such as gabardine, such as with cotton or texturized polyester, or blended fabrics. In some embodiments, the flexible printed circuit board 1830 is coupled to a sensor that is housed in the sensor attachment portion 1750. In some embodiments, the flexible printed circuit board 1830 includes a flexible substrate and flexible conductors. In some embodiments, the flexible substrate includes a Polyimide (PI), TPU, or a Thermoplastic Elastomer (TPE). In some embodiments, the flexible conductor includes copper or a stretchable conductive ink. In some embodiments, the elastic polymer sheet 1830 includes TPU. In some embodiments, the combination of layers described above causes the sensor attachment portion 1750 to operate as described herein. In some embodiments, different combinations of layers may be present and/or the layers may be arranged in a different sequence than that described above.

In some embodiments, the garment 100 includes one of the flexible sensor mounts 122 for each of the sensors 140. In some embodiments, the garment 100 includes one of the flexible sensor mounts 122 for some, but not all, of the sensors 140. In some embodiments, the garment 100 includes a standard rigid sensor mount (not shown in detail herein) for at least one of the sensors 140, whereby the at least one of the sensors mounted in a rigid sensor mount is not movable with respect to the first or second sensor attachment portion 120 or 130 in the manner described above. In some embodiments, the garment 100 includes one of the flexible sensor mounts 122 for each of the sensors 140 that is the first type of sensor (e.g., an acoustic sensor) and includes a rigid sensor mount for each of the sensors 140 that is the second type of sensor (e.g., a bio-potential sensor). Without intending to be limited by any particular theory, such an arrangement (i.e., in which acoustic sensors are attached using flexible sensor mounts while bio-potential sensors are attached using rigid sensor mounts) may be appropriate because an acoustic sensor requires full contact with skin around its entire periphery, while a bio-potential sensor does not require full contact in this manner.

Figure 7:
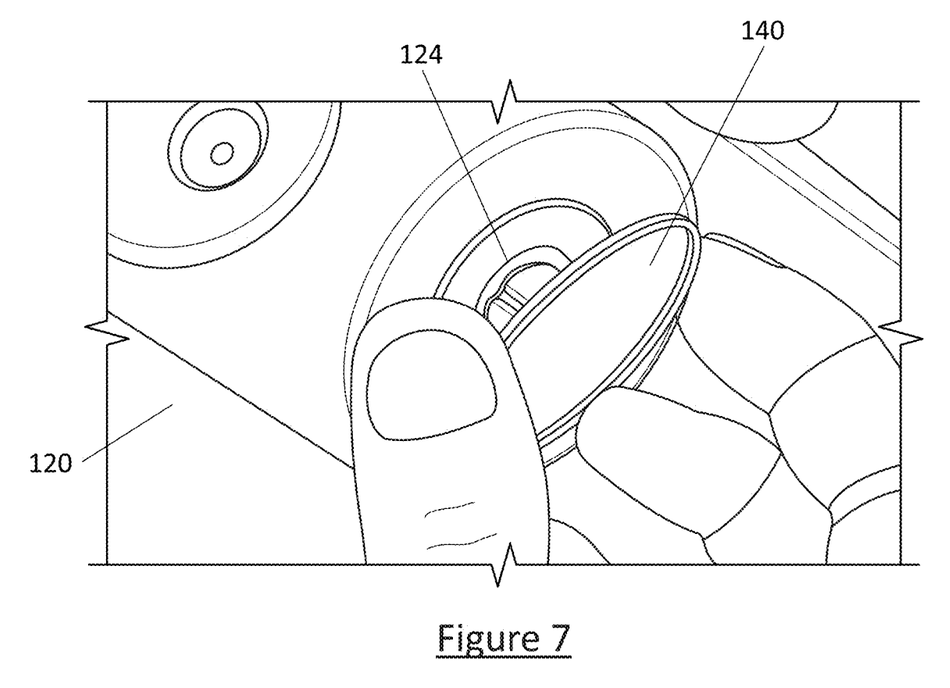
FIG. 7 shows a sensor being positioned in the sensor mount of FIG. 6.
Figure 8:
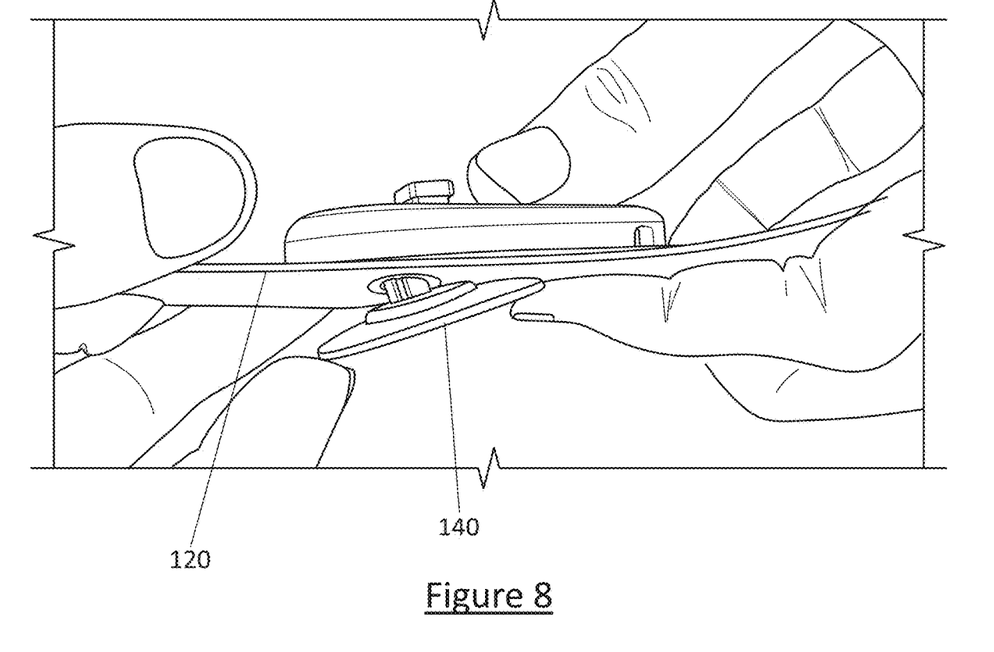
FIG. 8 shows the sensor and sensor mount of FIG. 7, the sensor being shown manually deflected.
Figure 9:
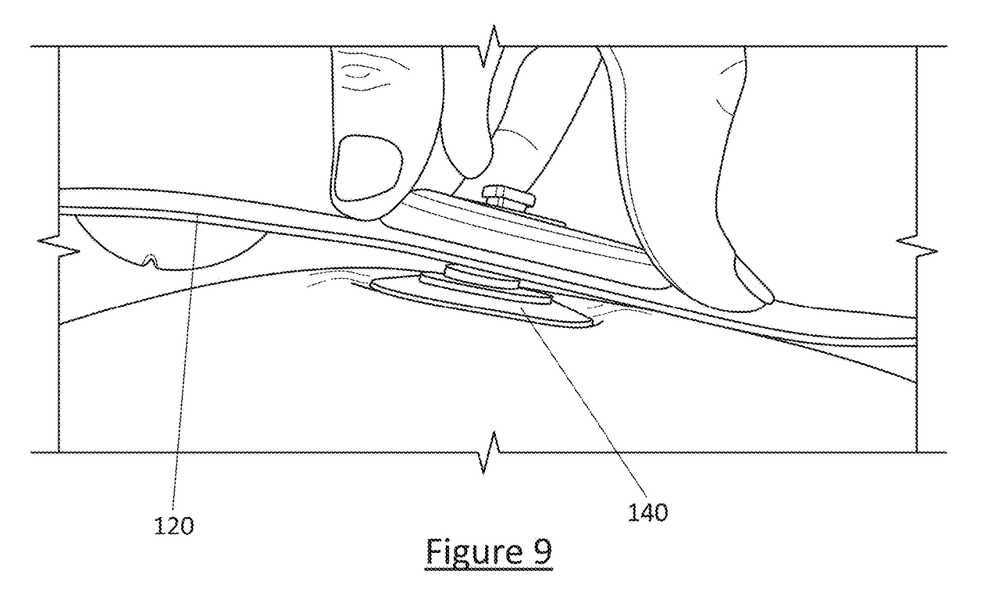
FIG. 9 shows the sensor and sensor mount of FIG. 7, the sensor being shown deflected due to being positioned in proximity to a simulated wearer.

FIG. 7 shows one of the sensors 140 being positioned within the flexible sensor mount 122. In some embodiments, when one of the sensors 140 is positioned within the flexible sensor mount 122, the sensor 140 and the rigid portion 124 are fixed in position with respect to one another, the inner region 127 of the flexible portion 126 is fixed with respect to the rigid portion 124, the outer region 128 of the flexible portion 126 is fixed with respect to the remainder of the first sensor attachment portion 120, and the flexible portion 126 is deformable such that the inner region 127 of the flexible portion 126 moves with respect to the outer region 128 of the flexible portion 126. Consequently, in some embodiments, each flexible sensor mount 122, the flexible sensor mount 122 allows one of the sensors 140 that is mounted therein to move with respect to the first sensor attachment portion 120. FIG. 8 shows the sensor 140 as positioned in the rigid portion 122 and manually rotated with respect to the sensor attachment portion 120. FIG. 9 shows the sensor 140 as positioned in the rigid portion 122 and rotated with respect to the sensor attachment portion 120 due to its position against a simulated wearer. In both FIG. 8 and FIG. 9, the rotation of the sensor 140 is allowed by the flexibility of the flexible portion 126.

Figure 10:
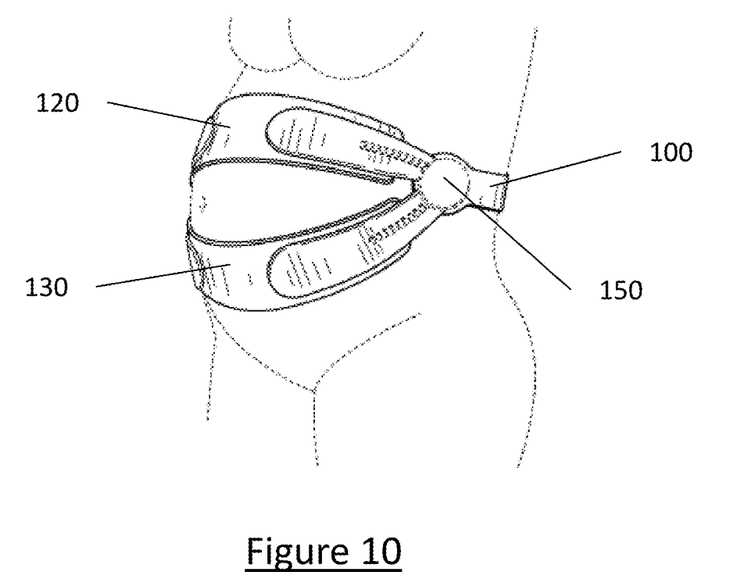
FIG. 10 shows a garment according to an exemplary embodiment, the garment being worn by a wearer having a comparatively small abdomen such that sensor attachment portions of the garment are positioned comparatively close to one another.
Figure 11:
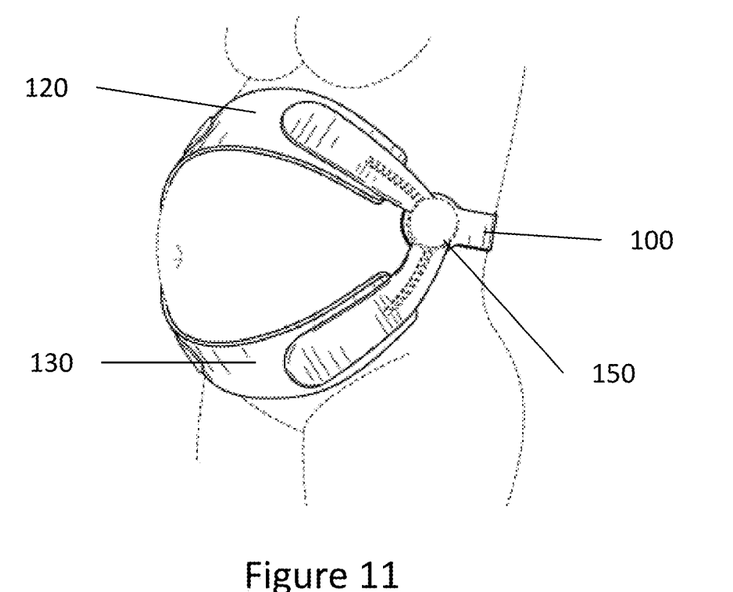
FIG. 11 shows the garment of FIG. 10, the garment being worn by a wearer having a comparatively large abdomen such that sensor attachment portions of the garment are positioned comparatively far from one another.

FIGS. 10 and 11 show an embodiment of the garment 100 as worn by pregnant mothers having differently sized abdomens. FIG. 10 shows an embodiment of the garment 100 as worn by a pregnant mother having a comparatively smaller abdomen. FIG. 11 shows an embodiment of the garment 100 as worn by a pregnant mother having a comparatively larger abdomen. In some embodiments, the garment 100 (i.e., the securing portion 110, the first sensor attachment portion 120, the second sensor attachment portion 130, the first hinge portion 150, and the second hinge portion 160) are configured such that, when the garment 100 is donned by a pregnant mother and the securing portion 110 and the first and second sensor attachment portions 120, 130 are secured and tightened so as to fit snugly about the wearer's abdomen, the positions of the first and sensor attachment portions 120, 130 will come to an equilibrium in which they, and the sensors 140 attached thereto, will anatomically follow the curvature of the wearer's abdomen, such that they are flush with the wearer's abdomen (i.e., the first and second sensor attachment portions 120, 130 self-adjust). In some embodiments, such adjustment is facilitated by the flexible portions 124 in which the sensors 140 are mounted. Consequently, as may be seen in FIGS. 10 and 11, when the garment 100 is donned by a pregnant mother having a comparatively smaller abdomen, the first and sensor attachment portions 120, 130 will be positioned comparatively close to one another, and when the garment 100 is donned by a pregnant mother having a comparatively larger abdomen, the first and second sensor attachment portions 120, 130 will be positioned comparatively far from one another.

In some embodiments, at least one of the elements described herein is made from a plastic material. In some embodiments, at least one of the elements described herein is made from Acrylonitrile Butadiene Styrene ("ABS") plastic. In some embodiments, at least one of the elements described herein is made from a polycarbonate plastic. In some embodiments, at least one of the materials described herein is made from one of the polycarbonate plastics commercialized under the trademark MAKROLON® by Bayer MaterialScience AG of Leverkusen, Germany. In some embodiments, at least one of the elements described herein is made from a nylon plastic.

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

What is claimed is:

1. A garment,
wherein the garment is a self-adjusting garment that is configured to be worn by a pregnant human subject during a course of pregnancy and to self-adjust positioning of at least one sensor integrated into the garment during the course of pregnancy;
wherein the garment comprises:
a securing portion operable to removably secure the garment about an abdomen of a wearer;
at least one sensor attachment portion pivotably attached to the securing portion, each of the at least one sensor attachment portion including at least one flexible sensor mount configured to receive and retain a sensor therein, wherein the at least one flexible sensor mount comprises:
a flexible portion including an elastomeric material and having an opening formed therein, wherein the opening in the elastomeric material is configured to maintain a sensor in a desired location when the garment is worn by the pregnant human subject, and
a rigid portion positioned within the opening of the flexible portion, wherein the rigid portion is configured to receive a sensor; and
at least one sensor, each of the at least one sensor being received in a corresponding one of the at least one flexible sensor mount of the at least one sensor attachment portion;
wherein the securing portion and the at least one sensor attachment portion are configured such that, when the securing portion is secured around a back of a wearer, the at least one sensor attachment portion pivots with respect to the securing portion so as to self-position the at least one sensor attachment portion across (a) an upper portion of the wearer's abdomen or (b) a lower portion of the wearer's abdomen, and
wherein each of the at least one flexible sensor mount is configured so as to orient a sensor received therein so as to be continuously flush with skin of the wearer when the garment is worn by the wearer and self-adjusts during the course of pregnancy.

2. The garment of claim 1, wherein the at least one sensor comprises at least one electrode.

3. The garment of claim 1, wherein the at least one sensor comprises at least one acoustic sensor.

4. The garment of claim 1, wherein the at least one sensor attachment portion includes two sensor attachment portions.

5. The garment of claim 4, wherein a first one of the sensor attachment portions is configured to extend around an upper portion of the abdomen of the wearer and a second one of the sensor attachment portions is configured to extend around a lower portion of the abdomen of the wearer.

6. The garment of claim 1, wherein each of the sensor attachment portions includes a plurality of the flexible sensor mounts, wherein the at least one sensor includes a plurality of sensors, and wherein each of the plurality of sensors is received within a corresponding one of the plurality of flexible sensor mounts.

7. The garment of claim 6, wherein each of the sensor attachment portions includes five sensor mounts.

8. The garment of claim 1, further comprising at least one hinge, each of the at least one hinge connecting an end of the securing portion to an end of the at least one sensor attachment portion.

9. The garment of claim 8, wherein the at least one hinge includes a sensor.

10. The garment of claim 8, wherein the at least one hinge includes two hinges, wherein a first one of the hinges connects a first end of the securing portion to a first end of the at least one sensor attachment portion, and wherein a second one of the hinges connects a second end of the securing portion to a second end of the at least one sensor attachment portion.

11. The garment of claim 10, wherein the at least one sensor attachment portion includes two sensor attachment portions, wherein the first one of the hinges connects a first end of the securing portion to (a) a first end of a first one of the sensor attachment portions and (b) a first end of a second one of the sensor attachment portions, and wherein a second one of the hinges connects a second end of the securing portion to (a) a second end of a first one of the sensor attachment portions and (b) a second end of a second one of the sensor attachment portions.

12. The garment of claim 1, wherein the elastomeric material is a viscoelastic material having a spring coefficient of between 1 N/mm and 20 N/mm.

13. The garment of claim 1, wherein each of the at least one sensor mount is configured to orient a sensor received therein so as to be flush with the skin of the wearer.

14. A method for positioning at least one sensor so as to be flush with skin on an abdomen of a wearer, the method comprising:
providing a garment including:
a securing portion operable to removably secure the garment about an abdomen of a wearer;
at least one sensor attachment portion pivotably attached to the securing portion, each of the at least one sensor attachment portion including at least one flexible sensor mount configured to receive and retain a sensor therein, wherein the at least one flexible sensor mount comprises:
a flexible portion including an elastomeric material and having an opening formed therein, wherein the opening in the elastomeric material is configured to maintain a sensor in a desired location when the garment is worn by the pregnant human subject, and
a rigid portion positioned within the opening of the flexible portion, wherein the rigid portion is configured to receive a sensor;
at least one sensor, each of the at least one sensor being received in a corresponding one of the at least one flexible sensor mount of the at least one sensor attachment portion;
wherein the securing portion and the at least one sensor attachment portion are configured such that, when the securing portion is secured about a back of a wearer, the at least one sensor attachment portion pivots with respect to the securing portion so as to extend around (a) an upper portion of the wearer's abdomen or (b) a lower portion of the wearer's abdomen, and
wherein each of the at least one sensor mount is configured so as to orient a sensor received therein so as to be flush with skin of the wearer when the garment is worn by the wearer;
positioning the garment so as to encircle a midsection of the wearer such that the securing portion extends around the back of the wearer and the at least one sensor attachment portion extends around an abdomen of the wearer;

securing the securing portion so as to retain the garment encircling the midsection of the wearer, whereby the at least one sensor attachment portion is positioned around one of an upper portion of an abdomen of the wearer and a lower portion of an abdomen of the wearer, and whereby the at least one flexible sensor mount flexes so as to allow the one of the at least one sensor received therein to be positioned flush with skin of the wearer.

15. The method of claim 14, wherein the at least one sensor attachment portion includes two sensor attachment portions, and wherein, when the securing portion is secured, a first one of the sensor attachment portions is positioned around an upper portion of the abdomen of the wearer and a second one of the sensor attachment portions is positioned around a lower portion of an abdomen of the wearer.

16. The method of claim 14, wherein the wearer is a pregnant human.

17. The method of claim 14, wherein the at least one sensor includes ten sensors.

18. The method of claim 14, wherein the at least one sensor includes at least one electrode and at least one acoustic sensor.

* * * * *